United States Patent [19]

Leger et al.

[11] Patent Number: 5,374,635
[45] Date of Patent: Dec. 20, 1994

[54] FURO[3,2-B]PYRIDINES AND THIENO[3,2-B]PYRIDINES AS INHIBITORS OF LEUKOTRIENE BIOSYNTHESIS

[75] Inventors: Serge Leger, Dollard des Ormeaux, Canada; John H. Hutchinson, Philadelphia, Pa.

[73] Assignee: Merck Frosst Canada, Inc., Quebec, Canada

[21] Appl. No.: 37,862

[22] Filed: Mar. 29, 1993

[51] Int. Cl.$^5$ ............... C07D 491/048; C07D 495/04; A61K 31/435
[52] U.S. Cl. .................... 514/301; 514/302; 546/114; 546/115; 548/154
[58] Field of Search ............... 546/114, 115; 548/154; 514/301, 302, 368

[56] References Cited

U.S. PATENT DOCUMENTS

| | | | |
|---|---|---|---|
| 4,629,733 | 12/1986 | Muller et al. | 514/418 |
| 5,034,403 | 7/1991 | Effland et al. | 514/338 |
| 5,095,031 | 3/1992 | Brooks et al. | 514/419 |
| 5,190,968 | 3/1993 | Gillard et al. | 514/419 |

FOREIGN PATENT DOCUMENTS

| | | |
|---|---|---|
| 56398/86 | 10/1986 | Australia . |
| 166591 | 1/1986 | European Pat. Off. . |
| 181568 | 5/1986 | European Pat. Off. . |
| 200101 | 12/1986 | European Pat. Off. . |
| 275667 | 7/1988 | European Pat. Off. . |
| 279263 | 8/1988 | European Pat. Off. . |
| 419049 | 3/1991 | European Pat. Off. . |
| 1228848 | 4/1971 | United Kingdom . |
| WO 91/06537 | 5/1991 | WIPO . |
| WO 91/06538 | 5/1991 | WIPO . |
| WO 91/06539 | 5/1991 | WIPO . |
| 92/03132 | 3/1992 | WIPO . |

OTHER PUBLICATIONS

Sheinkman et al. Chem Ab., vol. 67, 54017 (1967).
Biniecki et al. Chem Ab., vol. 98, 197936 (1983).
Pakula et al., Chem Ab., vol. 105, 190835 (1986).

*Primary Examiner*—Bernard Dentz
*Attorney, Agent, or Firm*—Mollie M. Yang; David L. Rose

[57] ABSTRACT

Compounds having the formula I:

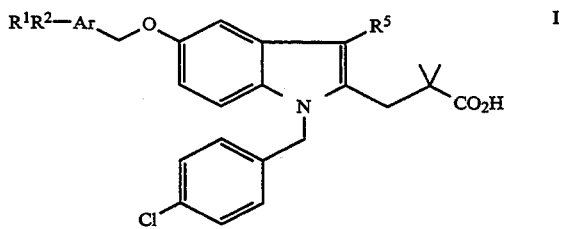

are inhibitors of leukotriene biosynthesis. These compounds are useful as anti-asthmatic, anti-allergic, anti-inflammatory, and cytoprotective agents. They are also useful in treating angina, cerebral spasm, glomemlar nephritis, hepatitis, endotoxemia, uveitis, and allograft rejection and in preventing the formation of atherosclerotic plaques.

11 Claims, No Drawings

FURO[3,2-B]PYRIDINES AND THIENO[3,2-B]PYRIDINES AS INHIBITORS OF LEUKOTRIENE BIOSYNTHESIS

CROSS-REFERENCE

The compounds of formula I' are described in U.S. Ser. No. 951,630, filed Sep. 25, 1992 now U.S. Pat. No. 4,308,850.

BACKGROUND OF THE INVENTION

European Patent Applications 166,591 and 275,667 disclose a series of indole-based compounds with activity as prostaglandin antagonists and inhibitors of leukotriene biosynthesis respectively. In EP 181,568 and EP 200,101 are disclosed a series of compounds, containing two aromatic nuclei, which are described as possessing activity as lipoxygenase inhibitors. In EP 279,263 is disclosed a series of indoles, benzofurans and benzothiophenes which are described as possessing activity as lipoxygenase inhibitors. U.S. Pat. No. 4,629,733 describes novel indolinones which are antithrombotic and inhibit both phosphodiesterase and tumor metastasis. The chemical preparation of quinolylindoles is referred to by Sheinkman, et al., Chem. Ab., Vol. 67, 54017 (1967), without mentioning any utility for such compounds. A number of N-acyl derivatives of indole-3-acetic acid are described as potential anti-inflammatory agents by Biniecki, et al., Chem. Ab., Vol. 98, 197936 (1983), by Pakula, etal., Chem. Ab., Vol. 105, 190835 (1986), and in British Pat. Spec. 1,228,848.

EP 419,049 (March 27, 1991) teaches (quinolin-2-ylmethoxy)indoles as inhibitors of leukotriene biosynthesis.

SUMMARY OF THE INVENTION

The present invention relates to furo[3,2-b]pyridines and thieno[3,2-b]pyridines having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, and anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

DETAILED DESCRIPTION OF THE INVENTION

The compounds of this invention are within the scope of Formula I':

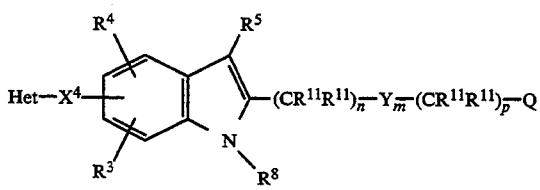

wherein:
Het is $ArR^1R^2$;

Ar is a bicyclic aromatic ring containing 8 or 9 members, one of which is O or S, and 0–2 of which is N, and the N-oxides thereof;

$R^1$, $R^2$, $R^3$, $R^4$ and $R^{10}$ are independently hydrogen, halogen, perhalo lower alkenyl, lower alkyl, lower alkenyl, lower alkynyl, $-CF_3$, $-CN$, $-NO_2$, $-N_3$, $-C(OH)R^{11}R^{11}$, $-CO_2R^{12}$, $-SR^{14}$, $-S(O)R^{14}$, $-S(O)_2R^{14}$, $-S(O)_2NR^{15}R^{15}$, $-OR^{15}$, $-NR^{15}R^{15}$, $-C(O)R^{16}$ or $-(CH_2)_rR^{21}$;

$R^5$ is hydrogen, $-CH_3$, $CF_3$, $-C(O)H$, $X^1$-$R^6$ or $X^2$-$R^7$;

$R^6$ and $R^9$ are independently alkyl, alkenyl, $-(CH_2)_uPh(R^{10})_2$ or $-(CH_2)_uTh(R^{10})_2$;

$R^7$ is $-CF_3$ or $R_6$;

$R^8$ is hydrogen or $X^3$—$R^9$;

each $R^{11}$ is independently hydrogen or lower alkyl, or two $R^{11}$'s on same carbon atom are joined to form a cycloalkyl ring of 3 to 6 carbon atoms;

$R^{12}$ is hydrogen, lower alkyl or $-CH_2R^{21}$;

$R^{13}$ is lower alkyl or $-(CH_2)_rR^{21}$;

$R^{14}$ is $-CF_3$ or $R^{13}$;

$R^{15}$ is hydrogen, $-COR^{16}$, $R^{13}$, or two $R^{15}$'s on the same nitrogen may be joined to form a monocyclic heterocyclic ring of 4 to 6 atoms containing up to 2 heteroatoms chosen from O, S, or N;

$R^{16}$ is hydrogen, $-CF_3$, lower alkyl, lower alkenyl, lower alkynyl or $-(CH_2)_rR^{21}$;

$R^{17}$ is $-(CH_2)_s-C(R^{18}R^{18})-(CH_2)_s-R^{19}$ or $-CH_2CONR^{15}R^{15}$;

$R^{18}$ is hydrogen or lower alkyl;

$R^{19}$ is a) a monocyclic or bicyclic heterocyclic ring containing from 3 to 9 nuclear carbon atoms and 1 or 2 nuclear hetero-atoms selected from N, S or O and with each ring in the heterocyclic radical being formed of 5 or 6 atoms, or b) the radical W—$R^{20}$;

$R^{20}$ is alkyl or $-COR^{23}$;

$R^{21}$ is phenyl substituted with 1 or 2 $R^{22}$ groups;

$R^{22}$ is hydrogen, halogen, lower alkyl, lower alkoxy, lower alkylthio, lower alkylsulfonyl, lower alkylcarbonyl, $-CF_3$, $-CN$, $-NO_2$ or $-N_3$;

$R^{23}$ is alkyl, cycloalkyl, or monocyclic monoheterocyclic ring;

$R^{24}$ is the residual structure of a standard amino acid, or $R^{18}$ and $R^{24}$ attached to the same N can cyclize to form a proline residue;

m is 0 or 1;

n is 0 to 3;

p is 1 to 3 when m is 1;

p is 0 to 3 when m is 0;

r is 0 to 2;

s is 0 to 3;

t is 0 to 2;

u is 0 to 3;

W is O, S or $NR^{15}$;

$X^1$ is O or $NR^{15}$;

$X^2$ is CO, $CR^{11}R^{11}$, S, S(O), or $S(O)_2$;

$X^3$ is CO, $CR^{11}R^{11}$, $S(O)_2$, or a bond;

$X^4$ is CH=CH, $CH_2$—$Y^1$, or $Y^1$—$CH_2$; Y is $X^1$ or $X^2$;

$Y^1$ is O, S, $S(O)_2$, or $CH_2$;

Q is $-CO_2R^{12}$, $-CONHS(O)_2R^{14}$, $-NHS(O)_2R^{14}$, $-S(O)_2NHR^{15}$, $-CONR^{15}R^{15}$, $-CO_2R^{17}$, $-CONR^{18}R^{24}$, $-CR^{11}R^{11}OH$, or 1H- or 2H-tetrazol-5-yl;

or a pharmaceutically acceptable salt thereof.

Specifically, the compounds of the present invention are of the Formula I:

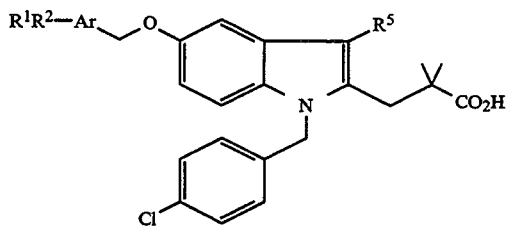

wherein:
$R^1$ and $R^2$ are independently H or Cl;
$R^5$ is H, lower alkyl or, —CO-lower alkyl;
Ar is furo[3,2-b]pyridin-5-yl, thieno[3,2,-b]pyridin-5-yl, or thieno[3,2-d]thiazol-2-yl,
or a pharmaceutically acceptable salt thereof.

DEFINITIONS

The following abbreviations have the indicated meanings:
Me=methyl
Bn=benzyl
Ph=phenyl
DIBAL-H=diisobutyl alumnium hydride
HMPA=hexamethylphosphorictriamide
KHMDS=potassium hexamethyldisilazide
t-Bu=tert-butyl
i-Pr=isopropyl
c-$C_6H_{11}$=cyclohexyl
c-Pr=cyclopropyl
c-=cyclo
Ac=acetyl
AIBN=2,2'-azobisisobutyronitrile
NBS=N-bromosuccinimide
NCS=N-chlorosuccinimide Alkyl, alkenyl, and alkynyl are intended to include linear, branched, and cyclic structures and combinations thereof.

"Lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

The pharmaceutical compositions of the present invention comprise a compound of Formula I as an active ingredient or a pharmaceutically acceptable salt, thereof, and may also contain a pharmaceutically acceptable carder and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

It will be understood that in the discussion of methods of treatment which follows, references to the compounds of Formula I are meant to also include the pharmaceutically acceptable salts.

The ability of the compounds of Formula I to inhibit biosynthesis of the leukotrienes makes them useful for inhibiting the symptoms induced by the leukotrienes in a human subject. This inhibition of the mammalian biosynthesis of leukotrienes indicates that the compotmds and pharmaceutical compositions thereof are useful to treat, prevent or ameliorate in mammals and especially in humans: 1) pulmonary conditions including diseases such as asthma, 2) allergies and allergic reactions such as allergic rhinitis, contact dermatitis, allergic conjunctivitis, and the like, 3) inflammation such as arthritis or inflammatory bowel disease, 4) pain, 5) skin conditions, such as atopic eczema and the like, 6) cardiovascular conditions such as angina, endotoxin shock, and the like and 7) renal insufficiency arising from ischaemia induced by immunological or chemical (cyclosporin) etiology, and that the compounds are cytoprotective agents.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about Img to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a nonsteroidal anti-inflammatory drug (NSAID) that might otherwise cause such damage (for example, indomethacin). For such use., the compound of Formula I is administered from 30 minutes prior up to 30 minutes after administration of the NSAID. Preferably it is administered prior to or simultaneously with the NSAID, (for example, in a combination dosage form).

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of Compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carder according to conventional pharmaceutical compounding techniques. The carder may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carders such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carders are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carder which constitutes one or more necessary ingredients. In general, the compositions are prepared by uniformly and intimately admixing the active ingredient with liquid carders or finely divided solid carders or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable tnachine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
| --- | --- |
| Compound of Formula I | 10 |
| Methylcellulose | 5.0 |

| -continued | |
|---|---|
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives;
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na+), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na+), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

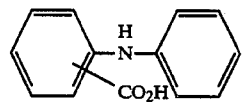

which can bear a variety of substituents and in which the free —COOH group can be in the form of a pharmaceutically acceptable salt group, e.g.,—COO⁻Na+.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

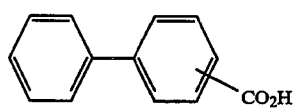

which can bear a variety of substituents and in which the free —COOH group can be in the form of a pharmaceutically acceptable salt group, e.g.,—COO⁻Na+.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

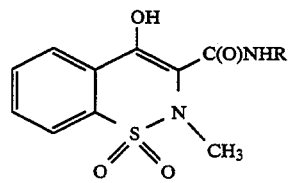

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopinoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyfidoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., *Pharmaprojects*), may also be used: 480156S, AA861, AD1590, AFP802, AFP860, A177B, AP504, AU8001, BPPC, BW540C, CHINOIN 127, CN100, EB382, EL508, F1044, GV3658, ITF182, KCNTE16090, KME4, LA2851, MR7 14, MR897, MY309, ONO3 144, PR823, PVi02, PV108, R830, RS2131, SCR152, SH440, SIR133, SPAS510, SQ27239, ST28 1, SY600 I, TA60, TAI-901 (4-benzoyl- 1 indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, fiurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotfienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981 ), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxy-chromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, Vol. 316, pages 126–131, 1985, and the like. Each of the references referred to in this paragraph is hereby incorporated herein by reference.

Other advantageous pharmaceutical compositions comprise the Formula I compounds in combination with anticholinergics such as ipratropium bromide, bronchodilators such as the beta agonist salbutamol, metaproterenol, terbutaline, fenoterol and the like, and the anti-asthmatic drugs theophylline, choline theophyllinate and enprofylline,the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

METHODS OF SYNTHESIS

Compounds of the present invention can be prepared according to the following methods.

Method A

The iodopyridine II (Aldrich Chemical Co.) reacts with trimethylsilylacetylene in the presence of copper(I) iodide and triphenylphosphine palladium(II) chloride complex to afford the furopyridine III, which is convened to IV by desilylation with hydrogen fluoride in the presence of pyridine or tetra-n-butyl amonium fluoride in THF. Treatment of IV with N-chlorosuccinimide or N-bromosuccinimide gives V.

Method B

Methyl ester VI is treated with an excess of a reducing reagent such as lithium aluminum hydride in a solvent like THF at 0° C. to afford the alcohol, which is oxidized with a reagent such as manganese dioxide to give aldehyde VII which is condensed with sodium pyruvate, followed by esterification with methanol in the presence of conc. hydrochloric acid to give methyl ester VIIIa. Chlorination of VIIIa with chlorine gas and silver sulfate in sulfuric acid affords 3-chlorothienopyridine VIIIb while chlorination of VIIIa with either sulfuryl chloride or trichloroisocyanuric acid affords 2,3-dichlorothienopyridine VIIIc. VIII are converted by reduction to the methyl ester with lithium aluminum hydride in a solvent like THF at 0° C. to the alcohols IX. Finally, IX is transformed into either a halogenated derivative or a sulfonate as a leaving group as exemplified by compound X.

Method C

Diacetate XI, prepared from tetrahydrothiophen-3-one according to literature procedures (C. Paulmier, Bull. Soc. Chim. Fr. (1979) 11,592), is heated in toluene at 200° C. to give thienothiazole XII. Treatment of XII with N-bromosuccinimide or N-chlorosuccinimide in a solvent like carbon tetrachloride affords the halogenated derivative XIII.

Method D

Compound V, X or XIII is reacted with phenol XIV (described in EP 419,049, Mar. 27, 1991) in the presence of a suitable base such as potassium or cesium carbonate in a suitable solvent such as acetone, acetonitrile, THF or DMF to yield compound XV which can be converted to its carboxylic acid I by standard procedures.

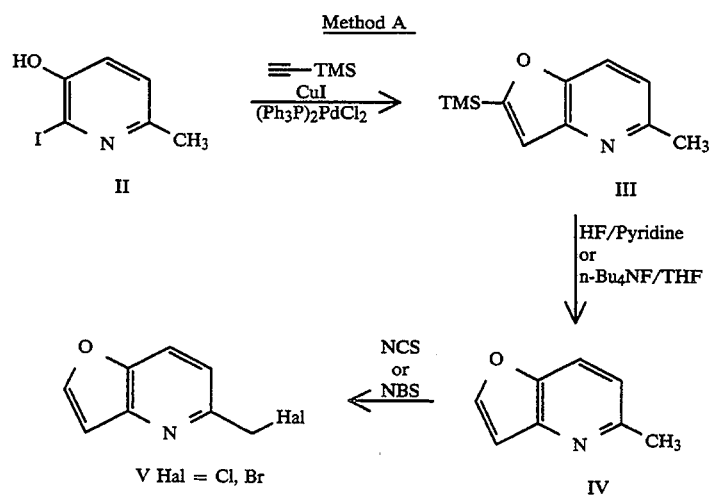

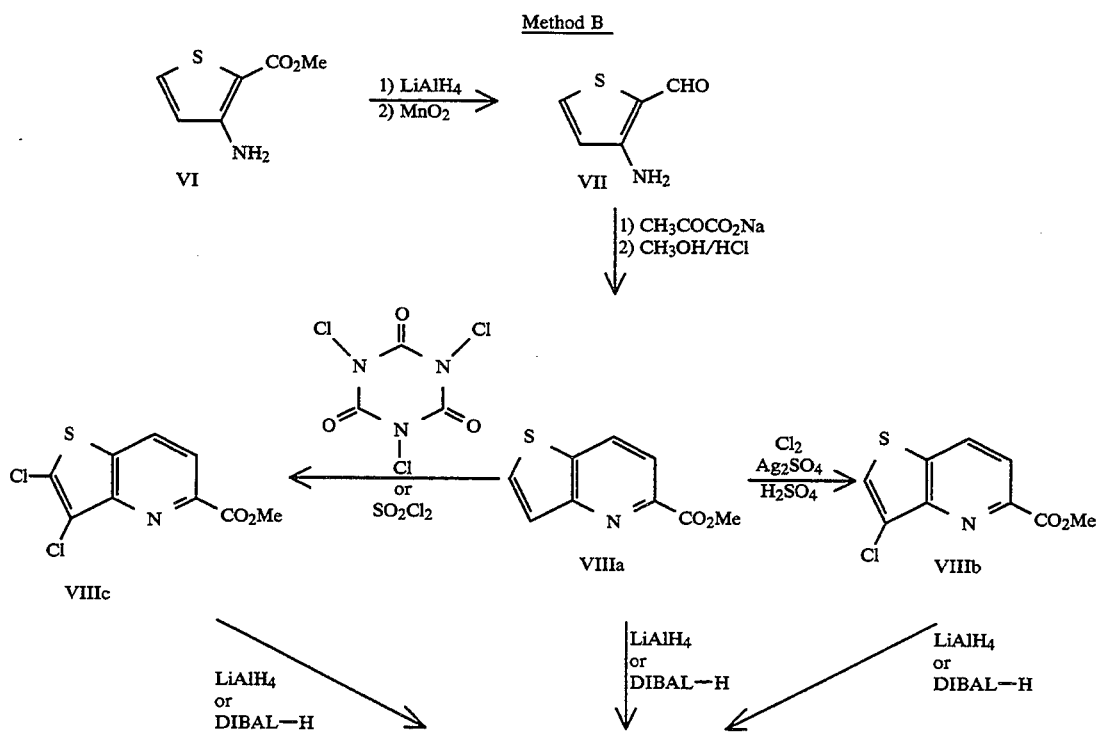

-continued
Method B

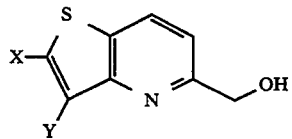

IX

↓ Sulfonation or halogenation

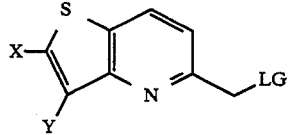

X where LG = —OSO₂—Me, —OSO₂—Ph—Me, Cl or Br

Method C

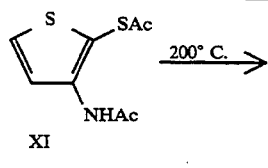

XI

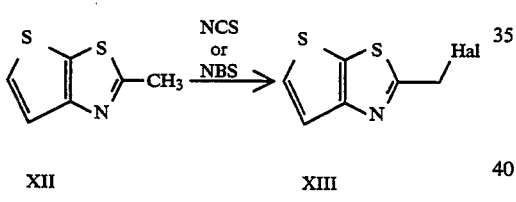

XII    XIII

Method D

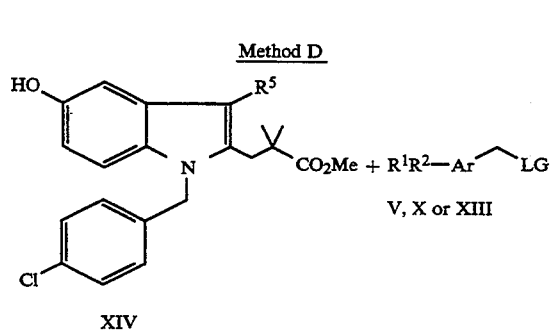

XIV

↓ Base

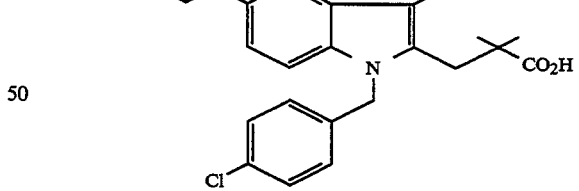

XV

-continued
Method D

↓ Hydrolysis

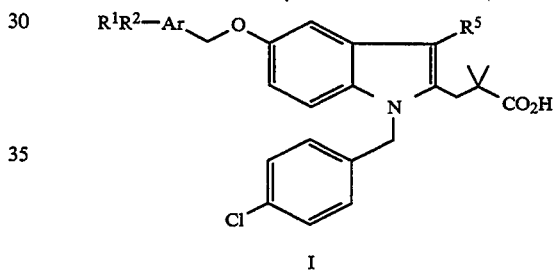

I

Representative Compounds

Table I illustrate compounds which are representative of the present invention.

TABLE 1

| Ex. No. | R¹/R² | Ar | R⁵ |
|---|---|---|---|
| 1 | H/H | Furo[3,2-b]pyridin-5-yl | H |
| 2 | H/H | Furo[3,2-b]pyridin-5-yl | Me |
| 3 | H/H | Furo[3,2-b]pyridin-5-yl | CO-t-Bu |
| 4 | H/H | Furo[3,2-b]pyridin-5-yl | CH₂-t-Bu |
| 5 | H/H | Thieno[3,2-b]pyridin-5-yl | H |
| 6 | H/H | Thieno[3,2-b]pyridin-5-yl | Me |
| 7 | H/H | Thieno[3,2-b]pyridin-5-yl | CO-t-Bu |
| 8 | H/H | Thieno[3,2-b]pyridin-5-yl | CH₂-t-Bu |
| 9 | 3-Cl/H | Thieno[3,2-b]pyridin-5-yl | H |
| 10 | 3-Cl/H | Thieno[3,2-b]pyridin-5-yl | CO-t-Bu |
| 11 | 3-Cl/H | Thieno[3,2-b]pyridin-5-yl | CH₂-t-Bu |
| 12 | 2-Cl/3-Cl | Thieno[3,2-b]pyridin-5-yl | H |
| 13 | 2-Cl/3-Cl | Thieno[3,2-b]pyridin-5-yl | CO-t-Bu |
| 14 | 2-Cl/3-Cl | Thieno[3,2-b]pyridin-5-yl | CH₂-t-Bu |
| 15 | H/H | Thieno[3,2-d]thiazol-2-yl | H |
| 16 | H/H | Thieno[3,2-d]thiazol-2-yl | Me |
| 17 | H/H | Thieno[3,2-d]thiazol-2-yl | CO-t-Bu |

TABLE 1-continued

[Chemical structure: indole with R¹R²-Ar-CH₂-O- substituent at 5-position, R⁵ at 3-position, CO₂H-bearing substituent at 2-position, and N-CH₂-(4-chlorophenyl) group]

| Ex. No. | R¹/R² | Ar | R⁵ |
|---------|-------|-----|-----|
| 18 | H/H | Thieno[3,2-d]thiazol-2-yl | CH$_2$-t-Bu |

Assays for Determining Biological Activity

Compounds of Formula I can be tested using the following assays to determine their mammalian leukotriene biosynthesis inhibiting activity.

Human 5-Lipoxygenase Inhibitor Screen

Objective of the Assay: The objective of the assay is to select agents which specifically inhibit the activity of human 5-lipoxygenase using a 100,000×g supernatant fraction prepared from insect cells infected with recombinant baculovirus containing the coding sequence for human 5-lipoxygenase. Enzyme activity is measured spectrophotometrically from the optimal rate of conjugated diene formation ($A_{234}$) measured after the incubation of the enzyme with arachidonic acid in the presence of ATP, calcium ions and phosphatidylcho line.

Description of Procedure: The activity of 5-lipoxygenase is measured using a spectrophotometric assay and recombinant human 5-lipoxygenase as a source of enzyme. The 100,000×g fraction from S19 cells infected with the recombinant baculovirus rvH5LO(8-1) containing the coding region sequence for human 5-lipoxygenase is prepared as described by Denis et al. (J. Biol. Chem., 266, 5072–5079 (1991)). The enzymatic activity is measured, using a spectrophoto-metric assay from the optimal rate of conjugated diene formation ($A_{234}$) using the procedure described by Riendeau et al. (Blochem. Pharmacol. 38, 2323–2321, (1989)) with minor modifications. The incubation mixture contains 50 mM sodium phosphate pH 7.4, 0.2 mM ATP, 0.2 mM CaCl$_2$, 20 gM arachidonic acid (5 μL from a 100-fold concentrated solution in ethanol), 12 μg/mL phosphatidylcholine, an aliquot of the 100,000×g fraction (2–10 gL) and inhibitor (0.5 mL final volume). Inhibitors are added as 500-fold concentrated solutions in DMSO. Reactions are initiated by the addition of an aliquot of the enzyme preparation and the rate of conjugated diene formation is followed for 2 minutes at room temperature. The reactions are performed in semi-micro cuvettes (0.7 mL capacity, 10 mm path length and 4 mm internal width) and the absorbance changes are recorded with a Hewlett-Packard diode array spectrophotometer (HP 8452A) connected to the ChemStation using UV/VIS Kinetics Software (Hewlett-Packard). Enzymatic activity is calculated from the optimal rate of the reaction by a linear fit of the variation of $A_{234}$ during the first twenty seconds using the least square method for the equation $A_{234} = V_o t + A_o$ where $V_o$ is the rate, t is the time, and $A_o$ is the absorbance at zero time. The results are expressed as percentages of inhibition of the reaction rate relative to controls (typically between 0.15–0.21 AU/min) containing the DMSO vehicle.

Rat Peritoneal Polymorphonuclear (PMN) Leukocyte Assays

Rats under ether anesthesia are injected (i.p.) with 8 mL of a suspension of sodium caseinate (6 grams in c—ga. 50 mL water). After 15–24 hr. the rats are sacrificed ($CO_2$) and the cells from the peritoneal cavity are recovered by lavage with 20 mL of buffer (Eagles MEM containing 30 mM HEPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/mL. A 500 μL aliquot of PMN suspension and test compound are preincubated for 2 minutes at 37° C., followed by the addition of 10 gM calcium ionophore A-23187. The suspension is stirred for an additional 4 minutes then bioassayed for LTB$_4$ content by adding an aliquot to a second 500 μL portion of the PMN at 37° C. The LTB$_4$ produced in the first incubation causes aggregation of the second PMN, which is measured as a change in light transmission. The size of the assay aliquot is chosen to give a submaximal transmission change (usually −70%) for the untreated control. The percentage inhibition of LTB$_4$ formation is calculated from the ratio of transmission change in the sample to the transmission change in the compound-free control.

Human Polymorphonuclear (PMN) Leukocyte LTB$_4$ Assay

A. Preparation of Human PMN. Human blood is obtained by antecubital venepuncture from consenting volunteers who have not taken medication within the previous 7 days. The blood is immediately added to 10% (v/v) trisodium citrate (0.13 M) or 5% (v/v) sodium heparin (1000 IU/mL). PMNs are isolated from anticoagulated blood by dextran sedimentation of erythrocytes followed by centrifugation through Ficoll-Hypaque (specific gravity 1.077), as described by Boyum (Scand. J. Clin. Lab. Invest., 21 (Supp 97), 77 (1968)). Contaminating erythrocytes are removed by lysis following exposure to ammonium chloride (0.16 M) in Tris buffer (pH 7.65), and the PMNs are resuspended at $5 \times 10^5$ cells/mL in HEPES (15 mM)-buffered Hanks balanced salt solution containing $Ca^{2+}$ (1.4 mM) and $Mg^{2+}$ (0.7 mM), pH 7.4.

B. Generation and Radioimmunoassay of LTB$_4$. PMNs (0.5 mL; $2.5 \times 10^5$ cells) are placed in plastic tubes and incubated (37° C., 2 min) with test compounds at the desired concentration or vehicle (DMSO, final concentration 0.2%) as control. The synthesis of LTB$_4$ is initiated by the addition of calcium ionophore A23187 (final concentration 10 μM) or vehicle in control samples and allowed to proceed for 5 minutes at 37° C. The reactions are then terminated by the addition of cold methanol (0.25 mL) and samples of the entire PMN reaction mixture are removed for radioimmunoassay of LTB$_4$.

Samples (50 gL) of authentic LTB$_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes. Thereafter [$^3$H]-LTB$_4$ (10 nCi in 100 μL RIA buffer) and LTB4-antiserum (100 μL of a 1:3000 dilution in RIA buffer) are added and the tubes vortexed. Reactants are allowed to equilibrate by incubation overnight at 4° C. To separate antibody-bound from free LTB$_4$, aliquots (50 gL) of activated charcoal (3% activated charcoal in RIA buffer containing 0.25% Dextran T-70) are added, the tubes vortexed, and allowed to stand at room temperature for 10 minutes prior to centrifugation (1500×g; 10 min; 4° C.). The supernatants containing antibody-bound $LTB_4$ are decanted into vials and Aquasol 2 (4 mL) is added. Radioactivity is quantified by liquid scintillation spectrometry. The specificity of the antiserum and the sensitivity of the procedure have been described by Rokach et al., *Prostaglandins Leukotrienes and Medicine*, 13, 21 (1984). The amount of $LTB_4$ produced in test and control samples is calculated. Inhibitory dose-response curves am constructed using a four-parameter algorithm and from these the $IC_{50}$ values are determined.

Human Whole Blood Assay IN VITRO for $LTB_4$ Production

Fresh blood is collected in heparinized tubes by venipuncture from human volunteers. A 500 μL aliquot is incubated with one of the test compounds at final concentrations varying from 3 nM to 3 mM at 37° C. for 15 min. Drug stock solutions are made up in DMSO and 1 μL of the stock solution is added to each assay tube. The blood is then incubated with A23187 (in 5 gL autologous plasma, 25 μM final concentration) at 37° C. for 30 min. At the end of incabation, plasma is obtained (12,000×g, 15 min) and a 100 μL aliquot is added to 400 μL methanol for protein precipitation. The mixture is vortexed. centrifuged and the supematant stored at −70° C. until assayed for $LTB_4$ by standard RIA.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carded out in a clear plastic box with intemal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Buxco Electronics preamplifier (Buxco Electronics Inc., Sharon, Conn.). The preamplifier is connected to a Beckman Type R Dynograph and to a Buxco computer consisting of waveform analyser, Data Acquisition Logger with special software. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing Img EA and 200 mg aluminum hydroxide in saline. They are used between days 12 and 24 post sensitization. In order to eliminate the serotonin component of the response, rats are pretreated intravenously 5 minutes prior to aerosol challenge with 3.0 μg/kg of methysergide. Rats are then exposed to an aerosol of 3% EA in saline for exactly 1 minute, then their respiratory profiles are recorded for a further 30 minutes. The duration of continuous dyspnea is measured by the Buxco computer.

Compounds are generally administered either orally 2–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. The activity of compounds is determined in terms of their ability to decrease the duration of antigen-induced dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics in Trained Conscious Squirrel Monkeys—A Non-Invasive Technique Objective of the Assay: To assess pulmonary mechanics changes in the airways of conscious squirrel monkeys with the use of a double plethysmograph instead of thoracic catheterization of the pleural space as in the former invasive technique to measure airway resistance ($R_L$) and dynamic compliance ($C_{dyn}$). The non-invasive technique measures changes in the pulmonary parameter "specific airway resistance" (sRaw) which is defined as airway resistance×thoracic gas volume. Agonists like $LTD_4$ (50 μg/mL) or *Ascaris suum* antigen (1:25 dilution) aerosol challenge cause an increase in sRaw values, i.e., bronchoconstriction, and consequently allow the evaluation of specific antagonists against these agonists.

For evaluation of compounds in this model, monkeys are fasted ovemight and dosed the following moming. The compound is dissolved in 1% methocel solution and given orally at doses ranging from 1 to 0.003 mg/kg in a volume of 1 mL/kg in the home cage. Three hours later the monkeys are placed in a chair within a thoracic plethysmograph whilst the muzzle of the monkey is placed into a nasal plethysmograph. through which he breathes. Baseline values for sRaw (cm $H_2O$×sec.) are taken, and at 4 hr post compound administration the monkeys are challenged with an aerosol of the specific agonist. The aerosol is generated by an ultrasonic DeVilbiss nebulizer and administered to the monkeys in the nasal plethysmograph at a rate of 2 litres/minute with the aid of a Pulmo-Aide pump (DeVilbiss, 561 series) for 10 minutes. For data collection, a Buxco Electronics Inc. respiratory computer is utilized which facilitates continuous recording of pulmonary function changes and derives a value for sRaw for each animal.

Following challenge, each minute of data is calculated as a percent change from control values for specific airway resistance (sRaw). The results for each test compound are subsequently obtained for a minimum period of 60 minutes post challenge which are then compared to previously obtained historical baseline control values for that monkey. In addition, the overall values for 60 minutes post challenge for each monkey (historical baseline values and test values) are averaged separately and are used to calculate the overall percent inhibition of $LTD_4$ or *Ascaris* antigen response by the test compound. For statistical analysis, paired t-test is used (Reference: Pennock, B. E. et al., J. Appl. Physiol.: Respirat. Environ. Exercise Physiol. 46 (2). 399–406, 1979.

Prevention of Induced Bronchoconstriction in Allergic Sheep

A. Rationale. Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods. Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, NC) and b) they have previously responded to inhalation challenge with *Ascaris suum* with both an acute bronchoconstriction and a late bronchial obstruction (W. M. Abraham, et al., Am. Rev. Resp. Dis., 128,839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery. Systems: Aerosols of Ascaris suum extract (1:20) are generated using a disposable medical nebulizer (Raindrop®, Puritan Bennett), which produces an aerosol with a mass median aerodynamic diameter of 6.2 μM (geometric standard deviation. 2.1) as determined by an electric size analyzer (Model 3030; Thermal Systems, St. Paul, Minn.). The output from the nebulizer is directed into a plastic t-piece, one end of which is attached to the nasotracheai tube, the other end of which is conected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis.: A Kruskal-Wallis one way ANOVA test is used to compare the acute immediate responses to antigen and the peak late response in the controls and the drug-treated animals.

STAFFING MATERIALS

Phenol 1

Methyl 3-[1-(4-chlorobenzyl)-3-trimethylacetyl-5-hydroxyindol-2-yl]-2,2-dimethylpropanoate To a solution of methyl 3-[1-(4-chlorobenzyl)-3-trimethylacetyl-5-(quinolin-2-ylmethoxy)indol-2-yl]-2,2-dimethylpropanoate (EP 419,049, Mar. 27, 1991, Example 54, Step A) (11.5 g) in 150 mL DMF at 100° C. was added $CuCl_2 \cdot 2H_2O$ (4.9 g) in 26 mL $H_2O$. After 7 hours, the solution was cooled, poured onto aqueous $NH_4OAc$, and extracted with EtOAc. The organic phase was washed twice with $NH_4OAc$ (aq), washed with brine, dried ($MgSO_4$), and evaporated. Purification of the residue by chromatography on silica gel (8% EtOAc in toluene) gave the title compound as a brown gum.

Phenol 2

Methyl 3-[1-(4-Chlorobenzyl)-3-(2,2-dimethylpropyl)-5-hydroxyindol-yl]-2,2-dimethylpropanate Step 1: Methyl 3-[1-(4-chlorobenzyl)-3-(2,2-dimethylpropyl)-5-(quinolin-2-ylmethoxy) indol-2-yl]-2,2-dimethylpropanoate A mixture of methyl 3-[1-(4-chlorobenzyl)-3-trimethylacetyl-5-(quinolin-2-ylmethoxy) indol-2-yl]-2,2-dimethylpropanoate (EP 419,049; Example 54, Step A) (15.64 g), $ZnI_2$ (25.2 g), and $NaBH_3CN$ (16.4 g) in 210 mL dichloroethane was stirred using a mechanical stirrer at r.t. for 30 minutes and then at 73° C. for 3 hours. The reaction mixture was allowed to cool, poured onto $NH_4OAc$ (aq), and extracted (3×EtOAc). The organic phase was dried ($MgSO_4$), evaporated, and the residue chromatographed (silica gel; ether/hexane 1:3) to give the title compound as a solid.

Step 2: Methy 3-[1-(4-chlorobenzyl)-3-(2,2-dimethylpropyl) -5-hydroxyindol-2- yl]-2,2-dimethylpropanoate Following the procedure described for Phenol 1, but substituting the ester from Step 1 for methyl 3-[1-(4-chlorobenzyl)-3-trimethylacetyl-5-(quinolin-2-ylmethoxy)indol-2-yl]-2,2-dimethyl propanoate as starting material, the title compound was obtained as a solid.

Phenol 3

Methyl 3-[N-(p-chlorobenzyl)-5-hydroxyindol-2-yl]-2,2-dimethylpropanoate

The title compound was prepared as described in EP 419,049, Mar. 27, 1991, Example 8, Step A.

EXAMPLES

The invention is further defined by reference to the following examples, which are intended to be illustrative and nol limiting. All temperatures are in degrees Celsius.

Example 1

3-[1-(4-Chlorobenzyl)-5-(furo[3,2-b]pyridin-5-ylmethoxy)indol-2-yl]2,2-dimethylpropanoic Acid Step 1: 2-(Trimethylsilyl)-6-methylfuro[3,2-b]pyridine A mixture of 2-iodo-6-methylpyridine-3-ol (20 g, 85 mmol), CuI (2.1 g, 11 mmol), trimethylsilyl acetylene (23.4 g, 238 mmol) and bis(triphenylphosphine)palladium(II)chloride (5.37 g, 7.65 mmol) in $Et_3N$ (380 mL) was heated to reflux for 20 hr. The mixture was cooled and diluted with ether and filtered through celite. The flitrate was concentrated in vacuo and the residue was chromatographed on silica gel (eluted with 10% EtOAc in hexane) to give 15 g (86% ) of the title compound. $^1H$ NMR ($CD_3COCD_3$) δ 0.40 (9H, s), 2.54 (3H, s), 7.12 (1H, d, J=8 Hz), 7.14 (1H, s), 7.75 (1H, d, J=8 Hz).

Step 2: 5-Methylfuro[3,2-b]pyridine

To a solution of 2-trimethylsilyl-5-methylfurano[3,2b]pyridine (3.17 g, 15.4 mmol) in THF (31 mL) at 0° C. was added a solution of tetra-n-butylammonium fluoride 1.0M in THF (17.0 mL, 17.0 rmnol). The mixture was stirred at room temparature for 30 min. A solution of aqueous $NH_4OAc$ 25% w/v (150 mL) was added and the mixture was extracted with EtOAc. The organic layer was dried over $MgSO_4$ and concentrated. The resulting residue was purified by chromatography on silica gel eluted with 30 % EtOAc in hexane to give the title compound as a colorless oil.

$^1H$ NMR ($CD_3COCD_3$) δ 2.56 (3H, s), 6.90 (1H, d, J=2 Hz), 7.16 (1H, d, J=8 Hz), 7.76 (1 H, d, J=8 Hz), 8.04 (1H, d, J=2 Hz).

Step 3: 5-(Bromomethyl)furo[3,2-b]pyridine

To a solution of 1.46 g (11.0 mmol) of 5-methylfuro[3,2b]pyridine (from Step 2) and 100 mg AIBN in 35 mL of CC14 was added 2.1 g (11.6 mmol) of NBS. The mixture was stirred at 75° C. under radiation from a 150 W spot light for 1 hr. Another portion of NBS was added (1.0 g) and the reaction was allowed to proceed for another 1.5 hr. The reaction was allowed to cool to r.t., diluted with aqueous $NH_4OAc$ 25% w/v (150 mL) and the mixture was extracted with EtOAc. The organic layer was dried over $MgSO_4$ and concentrated. The resulting residue was purified by chromatography on silica gel eluted with 20–25 % EtOAc in hexane to give the title compound as a colorless oil.

$^1H$ NMR ($CD_3COCD_3$) δ 4.78 (2H, s), 7.03 (1H, d, J=2 Hz), 7.53 (1H, d, J=8 Hz), 7.93 (1H, d, J=8 Hz), 8.17 (1H, d, J=2 Hz).

Step 4: Methyl 3-[1-(4-Chlorobenzyl)-5-(furo[3,2-b]pyridin-5-ylmethoxy) indol-2-yl]-2,2-dimethylpropanoate A solution of 440 mg( 1.18 mmol) of methyl 3-[1-(4-chlorobenzyl) -5-hydroxyindol-2-yl]-2,2-dimethylpropanoate, 5(bromomethyl)furo[3,2-b]pyridine (274 mg (1.3 mmol) from Step 3), and 772 mg (2.4 mmol) of $Cs_2CO_3$ in 6 mL of acetonitrile was stirred at r.t. for 18 hr. The reaction was diluted with aqueous $NH_4OAc$ 25% w/v (50 mL) and the mixture was extracted with EtOAc. The organic layer was dried over $MgSO_4$ and concentrated. The resulting residue was purified by chromatography on silica gel eluted with 25–30 % EtOAc in hexane to give the title compound as a colorless gum.

$^1H$ NMR ($CD_3COCD_3$) δ 1.25 (6H, s), 3.02 (2H, s), 3.75 (3H, s), 5.27 (2H, s), 5.47 (2H, s) 6.23 (1H, s), 6.83( 1H, dd, J=7 Hz, J=2 Hz), 6.93 (2H, d, J=8 Hz), 7.03 (1H, d, J=2 Hz), 7.15–7.21 (2H, m) 7.29 (2H, d, J=8 Hz), 7.55(1H, d, J=8 Hz), 7.94 (1H, d, J=8 Hz), 8.14 (1H, d, J=2 Hz)

Step 5: 3-[1-(4-Chlorobenzyl)-5-(furo[3,2-b]pyridin-5-ylmethoxy) indol-2-yl]-2,2-dimethylpropanoic acid To a solution of 540 mg( 1.1 mmol) of the ester from Step 4 in THF (11 mL) and MeOH (5.5 mL) was added aqueous LiOH 1.0N (3 mL, 3 mmol). The resulting solution was heated at 50° C. for 5 hours. The reaction was diluted with aqueous $NH_4OAc$ 25% w/v (50 mL) and the mixture was extracted with EtOAc. The organic layer was dried over $MgSO_4$ and concentrated. The resulting residue was purified by crystallization in EtOAc/hexane (1:4, 30 mL) to give the title compound as a white solid; m.p. 157° C. The sodium salt was prepared by dissolving the acid in ethanol, adding one equivalent of aqueous NaOH, and freeze drying the resulting solution. The sodium salts of the remaining examples were prepared in the same way.

Anal. Calcd. for $C_{28}H_{24}ClN_2NaO_4·1.5H_2O$: C, 62.51; H, 5.06; N, 5.21

Found: C, 62.34; H, 5.09; N, 5.26.

EXAMPLE 3

3-[1 -(4-Chlorobenzyl)-5-(furo[3,2-b]pyridin-5-ylmethoxy)-3-(trimethylacetyl) indol-2-yl]-2,2-dimethylpropanoic acid Step 1: 3-[1-(4-Chlorobenzyl)-5-(furo[3,2-b]pyridin-5-ylmethoxy)-3-(trimethylacetyl) indol-2-yl]-2,2-dimethylpropanoic acid Following the procedure described in Example 1, Steps 4 and 5, but replacing the phenol from Step 4 by methyl 3-[1-(4-chlorobenzyl)-5-hydroxy-3-(trimethylacetyl)indol-2-yl]-2,2dimethylpropanoate as starting material, the title compound was obtained as a gum and purified by crystallization in EtOAc/hexane (1:4, 25 mL) to give a white solid; m.p. 160° C.

Anal. Calcd. for $C_{33}H_{32}ClN_2NaO_5·0.5H_2O$: C, 65.61; H, 5.51; N, 4.64

Found: C, 65.34; H, 5.50; N, 4.63.

EXAMPLE 4

3-[1-(4-Chlorobenzyl)-3-(2,2-dimethylpropyl)-5-(furo[3,2-b]pyridin-5-ylmethoxy) indol-2-yl]-2,2-dimethylpropanoic acid Following the procedure described in Example 1, Steps 4 and 5, but replacing the phenol from Step 4 by methyl 3-[1-(4-chlorobenzyl)-3-(2,2-dimethylpropyl)-5-hydroxyindol-2-yl]-2,2dimethylpropanoate as starting material, the title compound was obtained as a gum and purified by crystallisation in EtOAc/hexane (1:4, 20 mL) to give the title compound as a white solid; m.p. 172°–173° C.

Anal. Calcd. for $C_{33}H_{34}ClN_2NaO_4\cdot H_2O$: C, 66.16; H, 6.06; N, 4.68

Found: C, 66.47; H, 5.94; N, 4.75.

EXAMPLE 5

3-[1-(4-Chlorobenzyl)-5-(thieno[3,2-b]pyridin-5-ylmethoxy)-indol-2-yl]-2,2-dimethylpropanic acid Step 1: 3-Amino-2-formylthiophene To a cold (0° C.) stirring solution of lithium aluminum hydride in THF (380 mL, 1 M) was added methyl 3-amino-2-thiophenecarboxylate (30 g, 190 mmol) in small portions over a period of 30 min. The resulting mixture was stirred at 0° C. for 1 hr. Water (15 mL) was added dropwise very slowly followed by slow addition of aqueous NaOH (15 mL, 3.5 N). Then more water (43 mL) and THF (300 mL) was added. The mixture was stirred well for 30 rain then filtered through celite. The celite was washed with more THF. The flitrate was concentrated to an oil which was redissolved in 2 L of EtOAc. The EtOAc solution was dried over anhydrous $MgSO_4$ and filtered. The resulting solution of the crude 3-amino-2-hydroxymethylthiophene was then treated with $MnO_2$ (100 g). The mixture was stirred at r.t. for 20 hr and then filtered through celite. The flitrate was evaporated to give 23.3g (65 %) of the title compound.

$^1H$ NMR ($CDCl_3$) δ 6.10 (2H, br s), 6.54 (1H, d, J=5 Hz), 7.48 (1H, d, J=5 Hz), 9.57 (1H, s).

Step 2: Thieno[3,2-b]pyridine-5-carboxylic acid

To a solution of 3-amino-2-formylthiophene (10 g, 78 mmol) in EtOH (50 mL) was added a mixture of aqueous NaOH (50 mL, 5%) and sodium pyruvate (17.16 g, 156 mmol). The mixture was heated to 60° C. for 2 hr. The mixture was cooled and washed with $Et_2O$: EtOAc 1:1 and then acidified with 1 N HCl to pH 3 at 0° C. The mixture was filtered and the solid was air dried to give 10 g (71%) of the title compound.

$^1H$ NMR ($CD_3SOCD_3$) δ 7.68 (1H, d, J=5.5 Hz), 8.00 (1H, d, J=8.4 Hz), 8.28 (1H, d, J=5.5 Hz), 8.65 (1H, d, J=8.4 Hz)

Step 3: Methyl thieno[3,2-b]pyridine-5-carboxylate

To a cold solution of HCl (10%) in MeOH (10 mL) was added thieno[3,2-b]pyridine-5-carboxylic acid (1.0 g, 5.6 mmol, and the mixture heated to reflux for 2 hr. After cooling to r.t., half the solvent was removed by evaporation and the remainder was partitioned between EtOAc and $H_2O$. Solid $NaHCO_3$ was added until the system remained basic. Separation, drying and evaporation of the organic layer afforded 0.75 g (70%) of the title compound.

$^1H$ NMR ($CDCl_3$) δ 4.05 (3H, s), 7.72 (1H, d, J=5 Hz), 7.87 (1H, d, J =5 Hz), 8.13 (1H, d, J=8 Hz), 8.35 (1H, d, J=8 Hz).

Step 4: Thieno[3,2-b]pyridine-5-methanol

To a 0° C. solution of the methyl ester (604 mg, 3.12 mmol) of Step 3 in 12 mL of THF was added lithium aluminum hydride in two portions (140 and 40 mg, 3.69 and 1.05 mmol) over 2 hr. The reaction mixture was left 30 min at r.t after which time the solution wax quenched with an aqueous solution of sodium potassium tartrate 0.5M and the mixture extracted with EtOAc. The organic layer was dried over $MgSO_4$, and the solvent evaporated. The crude oil was purified by flash chromatography on silica eluted with EtOAc: Hexane 70–80% to give 350 mg (68%) of the title alcohol as a light yellow solid.

$^1H$ NMR ($CD_3COCD_3$) δ 4.48 (1 H, t, J=5 Hz), 4.80 (2H, d, J=5 Hz), 7.47 (1H, d, J=5 Hz), 7.50 (1H, d, J=7 Hz), 7.99 (1H, d, J=5 Hz), 8.38 (1H, d, J=7 Hz).

Step 5: 5-(Methanesulonyloxymethyl)thieno[3,2-b]pyridine

To a 0° C. solution of the alcohol (904 mg, 5.5 mmol) of Step 4 in 35 mL of $CH_2Cl_2$ and $Et_3N$ (1.9 mL, 13.6 mmol) was added methanesulfonyl chloride (0.64 mL, 8.3 mmol) over i min. The reaction mixture was left 10 min at r.t after which time the solution was quenched with aqueous $NH_4OAc$ 25% w/v (100 mL) and the mixture extracted with EtOAc. The organic layer was dried over $MgSO_4$, and the solvent evaporated. The crude oil was used as such in the following step.

$^1H$ NMR ($CD_3COCD_3$) δ 3.22 (3H, s), 5.45 (2H, s), 7.55 (2H, m), 8.10 (1H, d, J=5 Hz), 8.51 (1H, d, J=7 Hz).

Step 6: 3-[1-(4-Chlorobenzyl)-5-(thieno[3,2-b]pyridin-5-ylmethoxy) indol-2-yl]-2,2-dimethylpropanoic acid Following the procedure described in Example 1, Steps 4 and 5, but replacing the 5-(bromomethyl)-furo[3,2-b]pyridine from Step 4 by 5-(methanesulonyloxymethyl)thieno[3,2-b]pyridine as starting material, the title compound was obtained as a gum and purified by crystallisation in THF/hexane (1:4, 14 mL) to give a white solid: m.p. 203°–204° C. (d).

Anal. Calcd. for $C_{28}H_{24}ClN_2NaO_3S\cdot H_2O$: C, 61.70; H, 4.81; N, 5.14

Found: C, 61.35; H, 4.78; N, 5.16.

EXAMPLE 7

3-[1-(4-Chlorobenzyl)-5-(thieno[3,2-b]pyridin-5-ylmethoxy)-3-(trimethylacetyl) indol-2-yl]-2,2-dimethylpropanoic acid Following the procedure described in Example 5, Step 6. but replacing the phenol from Example 1, Step 4 by methyl 3-[1-(4-chlorobenzyl)-5-hydroxy-3-(trimethylacetyl)indol-2-yl]-2,2-dimethylpropanoate as starting material, the title compound was obtained as a gum and purified by crystallization in EtOAc/hexane (1:4, 25 mL) to give a white solid; m.p. 193°–194° C.

Anal. Calcd. for $C_{33}H_{32}ClN_2NaO_4S\cdot 0.5H_2$: C, 63.92; H, 5.36; N, 4.52

Found: C, 63.63; H, 5.34; N, 4.46.

EXAMPLE 8

3-[1 -(4-Chlorobenzyl)-3-(2,2-dimethylpropyl)-5-(thieno[3,2-b]pyridin5-ylmethoxy) indol-2-yl]-2,2-dimethylpropanoic acid Following the procedure described in Example 5, Step 6, but replacing the phenol from Example 1, Step 4 by methyl 3-[1-(4-chlorobenzyl)-3-(2,2-dimethylpropyl)-5-hydroxyindol-2-yl]-2,2dimethylpropanoate as starting material, the title compound was obtained as a gum and purified by crystallization in EtOAc/hexane (51:4) to give colorless crystals; m.p. 187°–188° C.

Anal. Calcd. for $C_{33}H_{34}ClN_2NaO_3S\cdot H_2O$: C, 64.43; H, 5.90; N, 4.55

Found: C, 64.64; H, 5.90; N, 4.60.

EXAMPLE 11

3-[1 -(4-Chlorobenzyl)-3-(2,2-dimethylpropyl)-5-(3-chlorothieno[3,2-b]pyridin-5-ylmethoxy)indol-2-yl]-2,2-dimethylpropanoic acid Step 1: Methyl 3-chlorothieno[3,2-b]pyridine-5-carboxylate To a solution of Ag$_2$SO$_4$ (3.20 g, 10.3 mmol) in conc. H$_2$SO$_4$ (30 mL) at 100° C. was added methyl thieno[3,2-b]pyridine-5-carboxylate (1.92 g, 9.9 mmol). Cl$_2$ was bubbled through the rapid stirring mixture over a period of 1.5 hr. The mixture was cooled and then poured into ice (150 mL)and extracted with EtOAc. The precipitated AgCl remained in the aqueous layer while the organic layer was washed once with aq. NaHCO$_3$, once with H$_2$O, dried over MgSO$_4$ and evaporated. The crude product was purified by crystallization in EtOAc/hexane (1:9) to give the title compound as a light yellow solid; m.p. 126°–127° C.

$^1$H NMR (CD$_3$COCD$_3$) δ 3.98 (3H, s), 8.18 (1H, d, J=8 Hz), 8.21 (1H, s), 8.68 (1H, d, J=8 Hz).

Step 2: 3-Chlorothieno[3,2-b]pyridine-5-methanol

Following the procedure described in Example 5, Step 4, but replacing the ester from Step 4 by methyl 3-chlorothieno[3,2b]pyridine-5-carboxylate as starting material, the title compound was obtained as a gum and purified by flash chromatography on silica gel eluted with EtOAc/hexane 30%.

$^1$H NMR (CD$_3$COCD$_3$) δ 4.58 (1H, t, J=5 Hz), 4.87 (2H, d, J=5 Hz), 7.63 (1H, d, J=7 Hz), 8.02 (1H, s), 8.45 (1H, d, J=7 Hz), Step 3: 5-(Methanesulfonyloxymethyl)-3-chlorothieno[3,2-b]pyridine Following the procedure described in Example 5, Step 5. but replacing the alcohol from Step 4 by 3-chlorothieno[3,2-b]pyridine-5-methanol as starting material, the title compound was obtained as an oil which was used as such in the following step.

$^1$H NMR (CD$_3$COCD$_3$) δ 3.28 (3H, s), 5.52 (2H, s), 7.68 (1H, d, J=7 Hz), 8.12 (1H, s), 8.58 (1H, d, J=7 Hz).

Step 4: 3-[1-(4-Chlorobenzyl)-3-(2,2-dimethylpropyl)-5-( 3-chlorothieno[3,2-b]pyridin-5-ylmethoxy)indol-2-yl]-2,2-dimethylpropanoic acid Following the procedure described in Example 8, but replacing the mesylate from Example 5, Step 6 by 5-(methanesulfonyloxymethyl)-3-chlorothieno[3,2-b]pyridine as starting material. the title compound was obtained as a gum and purified by crystallization in THF/hexane (1:6) to give a white solid; m.p. 185°–186° C.

Anal. Calcd. for C$_{33}$H$_{33}$Cl$_2$N$_2$NaO$_3$S·H$_2$O: C, 61.02; H, 5.43; N, 4.31

Found: C, 60.86; H, 5.62; N, 4.39.

EXAMPLE 14

3-[1-(4-Chlorobenzyl)-5-(2,3-dichlorothieno[3,2-b]pyridin-5-yl-methoxy) -3-(2,2-dimethylpropyl)indol-2-yl]-2,2-dimethylpropanoic acid Step 1.: Methyl 2,3-dichlorothieno[3,2-b]pyridine-5-carboxylate A mixture of methyl thieno[3,2-b]pyridine-5-carboxylate (0.20 g, 1.03 mmol) and trichloroisocyanuric acid (0.962 g, 4.14 mmol) was refluxed in CH$_3$CN for 16 hr. The solvent was removed and the crude solid was chromatographed on silica gel with 5% EtOAc in toluene as eluant to afford 0.189 g (70%) of the title compound.

$^1$H NMR (C$_6$D$_6$) δ 3.55 (3H, s), 6.75 (1H, d, J=6.5 Hz), 7.75 (1H, d, J =6.5 Hz).

Step 2: 2,3-Dichlorothieno[3,2-b]pyridine-5-methanol

To a −30° C. solution of the methyl ester (60 g, 230 mmol) of Step 1 in 2.2 L of THF was added diisobutylaluminum hydride (570 mmol) over 1 hr. The reaction mixture was brought to −25° C. and allowed to proceed for another 10 min. The reaction was quenched with an aqueous solution of sodium potassium tartrate (1750 mL of 30% w/v) and extracted with EtOAc. The organic phase was dried over Na$_2$SO$_4$, and the solvent evaporated. The crude product was swished in CH$_2$Cl$_2$ (100 mL) to give 42 g (78%) of the title alcohol as a light yellow solid.

$^1$H NMR (CDCl$_3$) δ 2.08 (1H, t, J=5 Hz), 3.3 (2H, d, J=5 Hz, 5.7 (1H, d, J=8 Hz), 6.4 (1H, d, J=8 Hz).

Step 3: 2,3-Chloro-5-(methanesulonyloxymethyl)-thieno[3,2-b]pyridine

Following the procedure described in Example 5, Step 5, but replacing the alcohol from Step 4 by 2,3-dichlorothieno[3,2-b]pyridine-5-methanol as starting material, the title compound was obtained as an oil which was used as such in the following step. $^1$H NMR (CD$_3$COCD$_3$) δ 3.28 (3H, s), 5.50 (2H, s), 7.68 (1H, d j=7 Hz), 8.53 (1 H, d, J=7 Hz).

Step 4: 3-[1-(4-Chlorobenzyl)-5-(2,3-dichloro-thieno[3,2-b]pyridin-5-ylmethoxy) -3-(2,2-dimethylpropyl)indol-2-yl]-2,2-dimethylpropanoic acid Following the procedure described in Example 8, but replacing the mesylate from Example 5, Step 6 by 2,3-dichloro-5.(methanesulonyloxymethyl)thieno[3,2-b]pyridine as starting material, the title compound was obtained as a gum and purified by crystallization in THF/hexane (1:3) to give a white solid; m.p. 223°–224° C. (d).

$^1$H NMR (CD$_3$COCD$_3$) δ 0.87 (9H, s), 1.20 (6H, s), 2.71 (2H, s), 3.14 (2H, s), 5.35 (2H, s), 5.47 (2H, s) 6.80 (2H, d, J=8.6 Hz), 6.83(1H, dd, J=8.8 Hz, J=2.5 Hz), 7.16 (1 H, d, J=2.4 Hz), 7.18 (1 H, d, J=8.9 Hz), 7.23 (2H, bd, J=8.6 Hz), 7.72 (1H, d, J=8.4 Hz) 8.42 (1H, d, J=8.4 Hz).

EXAMPLE 15

3-[1-(4-Chlorobenzyl)-5-(thieno[3,2-d]thiazole-2-ylmethoxy)indol-2-yl]2,2-dimethylpropanoic acid Step 1: 2-Methylthieno[3,2-d]thiazole A solution of 660 mg (3.1 mmol) of N-acetyl-2-(acetylthio)-3-thiophenamine in 8 mL of toluene was degassed in a Pyrex robe under high vaccuum. The robe was subsequently sealed under high vaccuum and heated at 205° C. for 5 hr. Chromatographic separation on silica gel using hexane/EtOAc (5:1) gave 440 mg (80%) of the title product.

$^1$H NMR (CDCl$_3$) δ 2.82 (3H, s),7.40 (2H, s).

Step 2: 2-(Bromomethyl)thieno[3,2-d]thiazole

Following the procedure described in Example 1, Step 3, but replacing the 5-methylfuro[3,2-b]pyridine in Step 2 by 2methylthieno[3,2-d]thiazole as starting material, the title compound was obtained as an oil and purified by flash chromatography on silica gel eluted with EtOAc/hexane (10%).

$^1$H NMR (CD$_3$COCD$_3$) δ 5.02 (2H, s), 7.45 (1H, d, J=5 Hz), 7.71 (1H, d, J=5 Hz).

Step 3: 3-[1-(4-Chlorobenzyl)-5-(thieno[3,2-d]thiazole-2-yl-methoxy) indol-2-yl]-2,2-dimethylpropanoic acid Following the procedure described in Example 1, Steps 4 and 5, but substituting the 5-(bromomethyl)-furo[3,2-b]pyridine in Step 4 by 2-(bromomethyl)-thieno[3,2-d]thiazole as starting material, the title compound was obtained as a gum and purified by flash chromatography on silica gel eluted with EtOAc/hexane/AcOH (25:75:0.5) to give a light yellow solid.

Anal. Calcd. for C$_{26}$H$_{22}$ClN$_2$NaO$_3$S$_2$·H$_2$O: C, 56.77; H, 4.54; N, 5.16

Found: C, 56.67; H, 4.39; N, 5.08.

EXAMPLE 17

3-[1-(4-Chlorobenzyl)-5-(thieno[3,2-d]thiazole-2-ylmethoxy)-3-(trimethylacetyl)indol-2-yl]-2,2-dimethylpropanoic acid Following the procedure described in Example 15. Step 3, but replacing the phenol from Example 1, Step 4 by methyl 3-[1-chlorobenzyl)-5-hydroxy-3-(trimethylacetyl)indol-2-yl]-2,2-dimethylpropanoate as starting material, the title compound was obtained as a gum and purified by flash chromatography on silica gel eluted with EtOAc/hexane/AcOH (25:75:0.5) to give a light yellow solid.

Anal. Calcd. for $C_{31}H_{30}ClN_2NaO_4S_2 \cdot H_2O$: C, 58.62; H, 5.08; N, 4.41

Found: C, 58.35; H, 5.10; N, 4.42.

EXAMPLE 18

3-[1-(4-Chlorobenzyl)-3-(2,2-dimethylpropyl)-5-(thieno[3,2-d]thiazole-2-ylmethoxy) indol-2-yl]-2,2-dimethylpropanoic acid Following the procedure described in Example 15. Step 3, but replacing the phenol from Example 1, Step 4 by methyl 3-[1-(4-chlorobenzyl)-3-(2,2-dimethylpropyl)-5-hydroxyindol-2-yl]-2,2-dimethylpropanoate as starting material, the title compound was obtained as a gum and purified by flash chromatography on silica gel eluted with EtOAc/hexane/AcOH (20:80:0.5) to give a white solid.

Anal. Calcd. for $C_{31}H_{32}ClN_2NaO_3S_2 \cdot H_2O$: C, 59.94; H, 5.52; N, 4.51

Found: C, 59.71; H, 5.57; N, 4.46.

What is claimed is:

1. A compound of the Formula I:

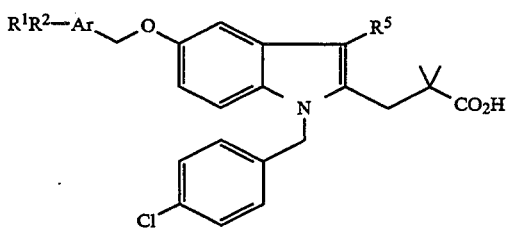

wherein:

$R^1$ and $R^2$ are independently H or Cl;

$R^5$ is H, lower alkyl or, —CO-lower alkyl;

Ar is furo[3,2-b]pyridin-5-yl, thieno[3,2,-b]pyridin-5-yl, or a pharmaceutically acceptable salt thereof.

2. A compound of claim 1 wherein the substituents are as follows:

| Ex. No. | $R^1/R^2$ | Ar | $R^5$ |
|---|---|---|---|
| 1 | H/H | Furo[3,2-b]pyridin-5-yl | H |
| 2 | H/H | Furo[3,2-b]pyridin-5-yl | Me |
| 3 | H/H | Furo[3,2-b]pyridin-5-yl | CO-t-Bu |
| 4 | H/H | Furo[3,2-b]pyridin-5-yl | $CH_2$-t-Bu |
| 5 | H/H | Thieno[3,2-b]pyridin-5-yl | H |
| 6 | H/H | Thieno[3,2-b]pyridin-5-yl | Me |
| 7 | H/H | Thieno[3,2-b]pyridin-5-yl | CO-t-Bu |
| 8 | H/H | Thieno[3,2-b]pyridin-5-yl | $CH_2$-t-Bu |
| 9 | 3-Cl/H | Thieno[3,2-b]pyridin-5-yl | H |
| 10 | 3-Cl/H | Thieno[3,2-b]pyridin-5-yl | CO-t-Bu |
| 11 | 3-Cl/H | Thieno[3,2-b]pyridin-5-yl | $CH_2$-t-Bu |
| 12 | 2-Cl/3-Cl | Thieno[3,2-b]pyridin-5-yl | H |
| 13 | 2-Cl/3-Cl | Thieno[3,2-b]pyridin-5-yl | CO-t-Bu |
| 14 | 2-Cl/3-Cl | Thieno[3,2-b]pyridin-5-yl | $CF_2$-t-Bu |
| 15 | H/H | Thieno[3,2-d]thiazol-2-yl | H |
| 16 | H/H | Thieno[3,2-d]thiazol-2-yl | Me |
| 17 | H/H | Thieno[3,2-d]thiazol-2-yl | CO-t-Bu |
| 18 | H/H | Thieno[3,2-d]thiazol-2-yl | $CH_2$-2-Bu |

3. A pharmaceutical composition comprising a therapeutically effective amount of a compound of claim 1 and a pharmaceutically acceptable carder.

4. A pharmaceutical composition of claim 3 additionally comprising an effective amount of a second active ingredient selected from the group consisting of non-steroidal anti-inflammatory drugs; peripheral analgesic agents; cyclooxygenase inhibitors; leukotriene antagonists; leukotriene biosynthesis inhibitors; $H_1$- or $H_2$-receptor antagonists; antihistaminic agents; prostaglandin antogonists; thromboxane antagonists; thromboxane synthetase inhibitors; and ACE antagonists.

5. A pharmaceutical composition of claim 4, wherein the second active ingredient is a non-steroidal anti-inflammatory drug.

6. A pharmaceutical composition comprising a therapeutically effective amount of a compound of claim 1, an effective amount of a second active ingredient which is a non-steroidal anti-inflammatory drug, and a pharmaceutically acceptable carrier, wherein the weight ratio of said compound of claim 1 to said second active ingredient ranges from about 1000:1 to 1: 1000.

7. A method of preventing the synthesis of leukotrienes in a mammal which comprises administering to said mammal an effective amount of a compound of claim 1.

8. A method of claim 7 wherein the mammal is man.

9. A method of treating asthma in a mammal comprising administering to a mammal in need of such treatment a therapeutically effective amount of a compound of claim 1.

10. A method of treating inflammatory diseases of the eye in a mammal which comprises administering to a mammal in need of such treatment a therapeutically effective amount of a compound of claim 1.

11. The method of claim 10 wherein the mammal is man.

* * * * *